US011813191B2

(12) United States Patent
Godinez et al.

(10) Patent No.: US 11,813,191 B2
(45) Date of Patent: *Nov. 14, 2023

(54) URINE COLLECTION DEVICE, SYSTEM, AND METHOD (71) Applicant: Medline Industries, LP, Northfield, IL (US)

(72) Inventors: Saul Godinez, Chicago, IL (US); Allison Peterson, Chicago, IL (US)

(73) Assignee: Medline Industries, LP, Northfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/968,987

(22) Filed: Oct. 19, 2022

(65) Prior Publication Data
US 2023/0045839 A1 Feb. 16, 2023

Related U.S. Application Data (63) Continuation of application No. 16/905,116, filed on Jun. 18, 2020, now Pat. No. 11,504,265.

(51) Int. Cl.
*A61F 5/455* (2006.01)
*A61F 5/44* (2006.01)
*A61F 5/443* (2006.01)
*A61M 1/00* (2006.01)

(52) U.S. Cl.
CPC .......... *A61F 5/455* (2013.01); *A61F 5/4401* (2013.01); *A61F 5/443* (2013.01); *A61M 1/84* (2021.05); *A61M 2202/0496* (2013.01)

(58) Field of Classification Search
CPC ........ A61F 5/455; A61F 5/4401; A61F 5/443; A61F 13/0203; A61F 13/0206; A61F 13/0216; A61F 2013/15146; A61F 13/15; A61F 13/5611; A61F 13/2042; A61F 13/26; A61F 13/266; A61M 1/84; A61M 2202/0496
See application file for complete search history.

(56) References Cited

U.S. PATENT DOCUMENTS

| | | | |
|---|---|---|---|
| 7,445,615 B2 | 11/2008 | Mizutani | |
| 8,454,570 B2 | 6/2013 | Carstens | |
| 2004/0236292 A1* | 11/2004 | Tazoe | A61F 5/451 604/317 |
| 2005/0137559 A1 | 6/2005 | Mizutani | |

(Continued)

*Primary Examiner* — Sarah Al Hashimi
*Assistant Examiner* — Hans Kaliher
(74) *Attorney, Agent, or Firm* — Fitch, Even, Tabin & Flannery LLP (57) ABSTRACT A urinary collection device includes an outer surface and a generally fluid-permeable core that communicates fluidically with an aspiration tube. The outer surface includes an obverse opening to allow urine to flow into the fluid-permeable core when the device is positioned supralabially. On the reverse may be an actuatable fastener configured to retain the device in a reverse-folded intralabial position. In this manner the device may be placed supralabially or intralabially for urine collection as appropriate. The core may include a first knit fabric layer and a second knit fabric layer joined by a plurality of fibers, the fibers being oriented generally to extend from an obverse to a reverse position to thereby result in flow channels through the core.

10 Claims, 12 Drawing Sheets

(56) References Cited

U.S. PATENT DOCUMENTS

2019/0142624 A1\* 5/2019 Sanchez ................ A61F 5/4405
 604/319
2021/0236323 A1\* 8/2021 Austermann ........... A61F 5/453
2021/0353450 A1\* 11/2021 Sharma .................. A61F 5/455

\* cited by examiner

URINE COLLECTION DEVICE, SYSTEM, AND METHOD

CROSS-REFERENCE TO RELATED APPLICATION

This application is a continuation of U.S. application Ser. No. 16/905,116 filed Jun. 18, 2020, the disclosure of which is incorporated in its entirety by reference herein.

TECHNICAL FIELD

The disclosure relates to the field of urine management, particularly in the health care and long-term care settings.

BACKGROUND

Urinary management is a critical need for both acute and long-term patient care. In the hospital setting, many patients, such as post-surgical patients, are unable to manage their urine flow during and immediately after surgery. A general solution to this issue is to catheterize the patient, using for example an indwelling catheter. Catheterization is advantageous when it is desired to monitor the urine output of a patient.

Catheterization is known to cause problems with nosocomial infections, and generally there are a high number of catheter-related urinary tract infections (CAUTI) annually. CAUTI is one of the most common nosocomial infections in hospitals and nursing homes, accounting for a major percentage of institutionally acquired infections. Catheterization also is an invasive procedure, albeit minimally.

To address the issues associated with catheterization, it is known to provide human urine aspiration systems that generally include an electric pump for applying suction to a urinal and for aspirating the urine to a storage canister. Generally, the patient is outfitted with a urinary collection device, sometimes also called a "catheter," that is secured at or near the patient. Upon activation of the pump, urine is caused to aspirate away from the patient and into the canister.

It is now desired to provide a female external urinary collection device and urine aspiration system, the urinary collection device being useful with known urinary aspiration systems. It has now been found that a urinary collection device, urinary collection device assembly method, and urinary aspiration system may be provided, along with a method of providing urinary management to a female. The urinary device generally comprises a flexible and generally fluid-impermeable outer surface having an obverse face and a reverse face, the device including a generally fluid-permeable core that communicates fluidically with an aspiration tube. The outer surface of the device includes an obverse opening to allow urine to flow into the fluid-permeable core when the device is positioned supralabially. The reverse face of the device in some embodiments includes an actuatable fastener configured to retain the device in a reverse-folded intralabial position upon actuation. In other embodiment, useful in connection with embodiments that include the actuatable fastener, the urinary collection device comprises a flexible and generally fluid-impermeable outer surface having an obverse face and a reverse face, and a generally fluid-permeable core that communicates fluidically with an aspiration tube. The core may comprise a first knit fabric layer and a second knit fabric layer joined by a plurality of fibers, the fibers being oriented generally to extend from an obverse to a reverse position to thereby result in flow channels through the core.

The device is intended for use with female patients, although it is contemplated that in some cases, particularly in an emergency context, the device alternatively could be used with male patients. An optional method of use includes evaluating a patient to determine whether to employ supralabial or intralabial urine collection, and placing the urinary collection device proximal the patient for urine collection, the method including actuating an actuatable fastener to retain the device in a reverse-folded intralabial position only if intralabial urine collection is elected. An optional system includes the device connected to a source of suction at the tube.

DETAILED DESCRIPTION

Figure 1:
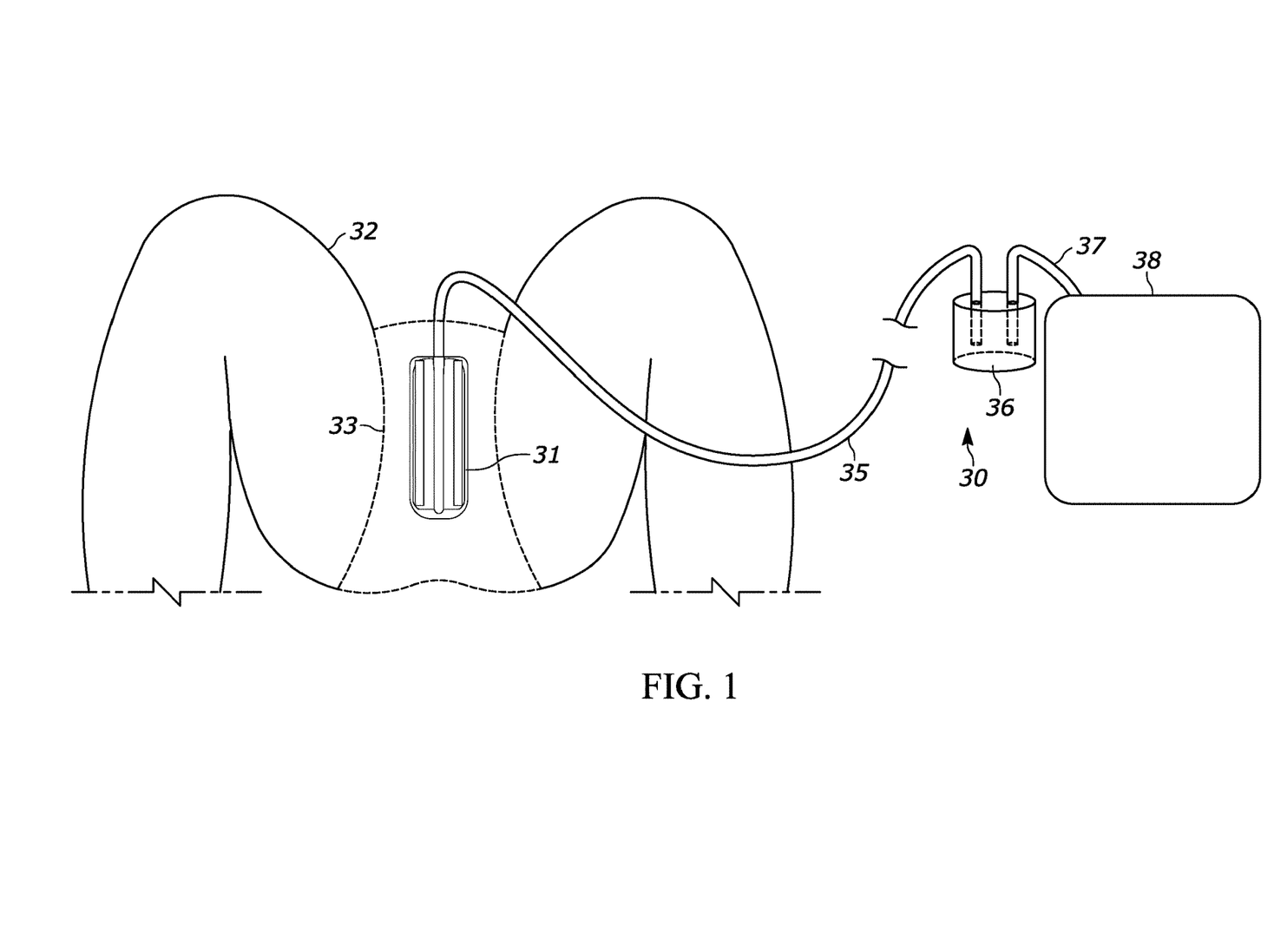
FIG. 1 is a perspective view illustrating an exemplary urinary collection device or "catheter" positioned proximal a female patient and illustrating schematically other components of a urinary aspiration system.
Figure 2:
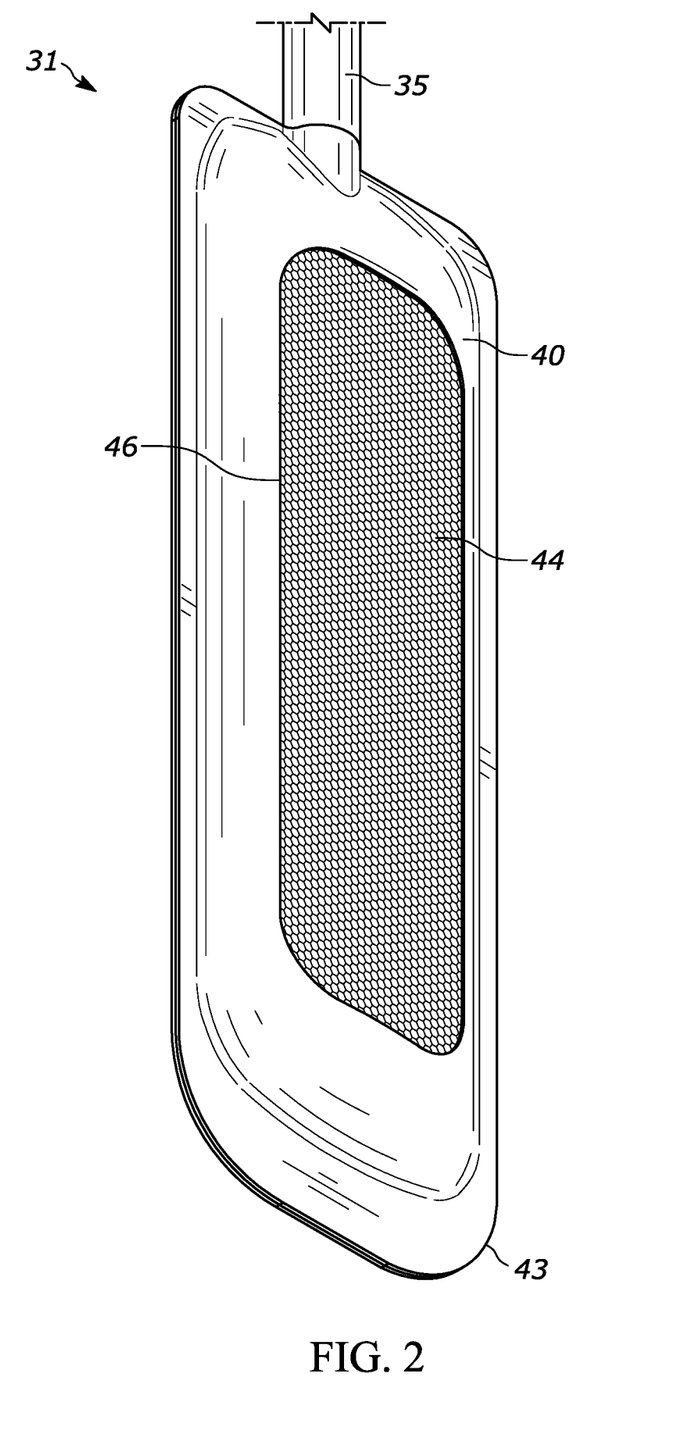
FIG. 2 is a perspective view of the urinary collection device illustrated in FIG. 1, the device being shown in an unfolded configuration.

With reference to FIG. 1, a urinary collection system 30 includes a urinary collection device 31 positioned in a supralabial position proximal the urethra of patient 32. The patient 32 in this embodiment is a female having relatively small labia. The device 31 may be secured to the patient via an optional belt (not shown) or adhesively to an undergarment 33 of the patient as hereafter described. The device 31 includes a tube 35 made of a suitable flexible material, typically polyvinyl chloride, that in use is connected to a source of suction. Conventionally, the tube 35 leads to a sealed canister 36 (shown schematically) and the sealed canister 36 is connected via another tube 37 to a source of suction 38 such as hospital house suction or a local suction pump. Preferably, the suction source is sufficient to provide a suction pressure of at least about 40 mm Hg in the tube. When the suction source 38 is actuated, suction is created in the tube 35 to thereby draw urine away from the urinary collection device 31 and into the canister 36. Periodically a clinician will monitor and empty the canister 36. The urine then may be simply discarded or may be measured, evaluated, or tested.

As seen in FIGS. 2-8, the urinary collection device 31 has an obverse face 40 that in use is positioned to face or connect the patient, and a reverse face 41 that is oriented away from the patient. The device is composed of an outer surface 43, a fluid-permeable core 44 (FIGS. 2 and 3), and the heretofore mentioned tube 35. The outer surface 43 includes an obverse opening 46 to allow urine to flow into the fluid-permeable core. The reverse face 41 of the device includes an actuatable fastener 48, shown in the illustrated embodiment as two backed adhesive strips 50, 51. The fluid-permeable core communicates fluidically with the tube 35, such that the tube 35 functions as an aspiration tube to allow withdrawal of urine away from the urinary collection device 31 via suction into the canister 36.

Figure 9:
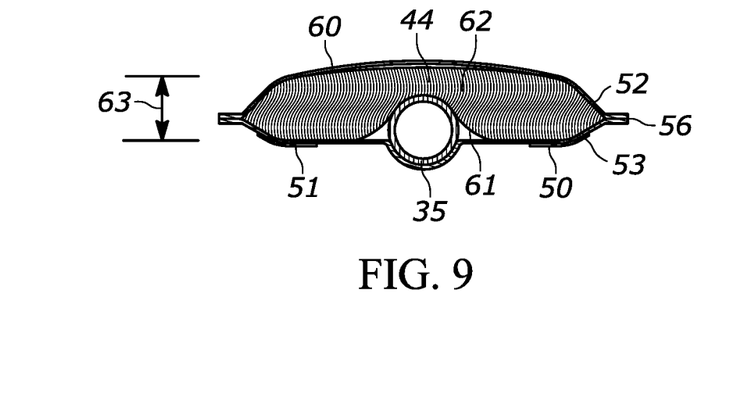
FIG. 9 is a cross-sectional view taken along line 9-9 in FIG. 3, illustrating internal structure of the core of the urinary collection device.
Figure 10:
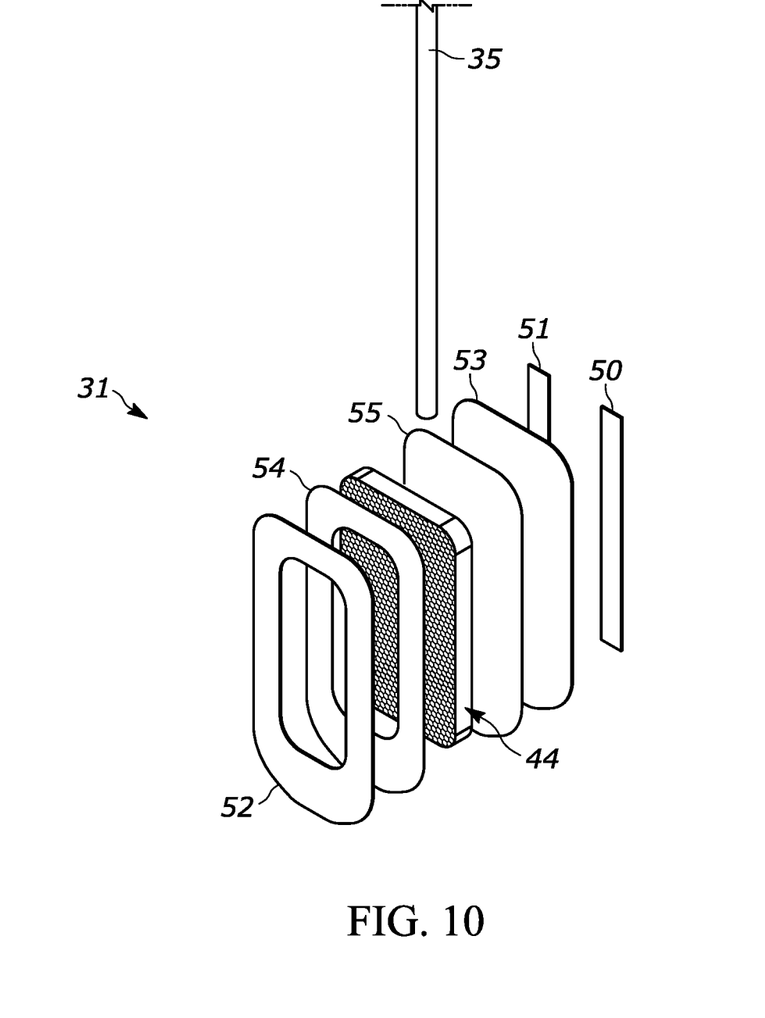
FIG. 10 is an exploded view of the urinary collection device.

With reference to FIG. 10, the device 31 may be composed of the core 44, an obverse outer layer 52, a reverse outer layer 53, and adhesive layers 54, 55. The obverse and reverse outer layers 52, 53 are fluid-impermeable at ordinary operating pressures. These layers may be composed of any suitable material and in some embodiments may be composed of polyethylene foam. As seen particularly with reference to FIG. 9, the obverse and reverse outer layers 52, 53 are joined at an outer seam 56 when adhesively secured together. The adhesive may be any suitable water-resistant adhesive, such as a polyacrylate adhesive.

With particular reference to FIG. 9, the core may compromise any fluid-permeable core material, but preferably comprises a mesh-type material comprising a first knit fabric layer 60, a second knit layer fabric 61, and a plurality of fibers 62 joining the first knit fabric layer and second knit fabric layer. The fibers 62 are oriented generally to extend from an obverse to a reverse position to thereby result in flow channels through the core. Ideally, the core has a height 63 (FIG. 9) of at least 10 millimeters and preferably a height ranging from 10-15 millimeters such that if the materials comprised the PVC tubing does not cause patient discomfort. One suitable material is a three-dimensional mesh material sold under the product designation T6010 by Müller Textil GMBH of Wiehl-Dravenderhoehe, Germany. Another suitable core material is T5975 also sold by Müller Textil. Plural layers of T5693 and TEN6197, currently offered in 6 millimeter heights, would be suitable.

Figure 3:
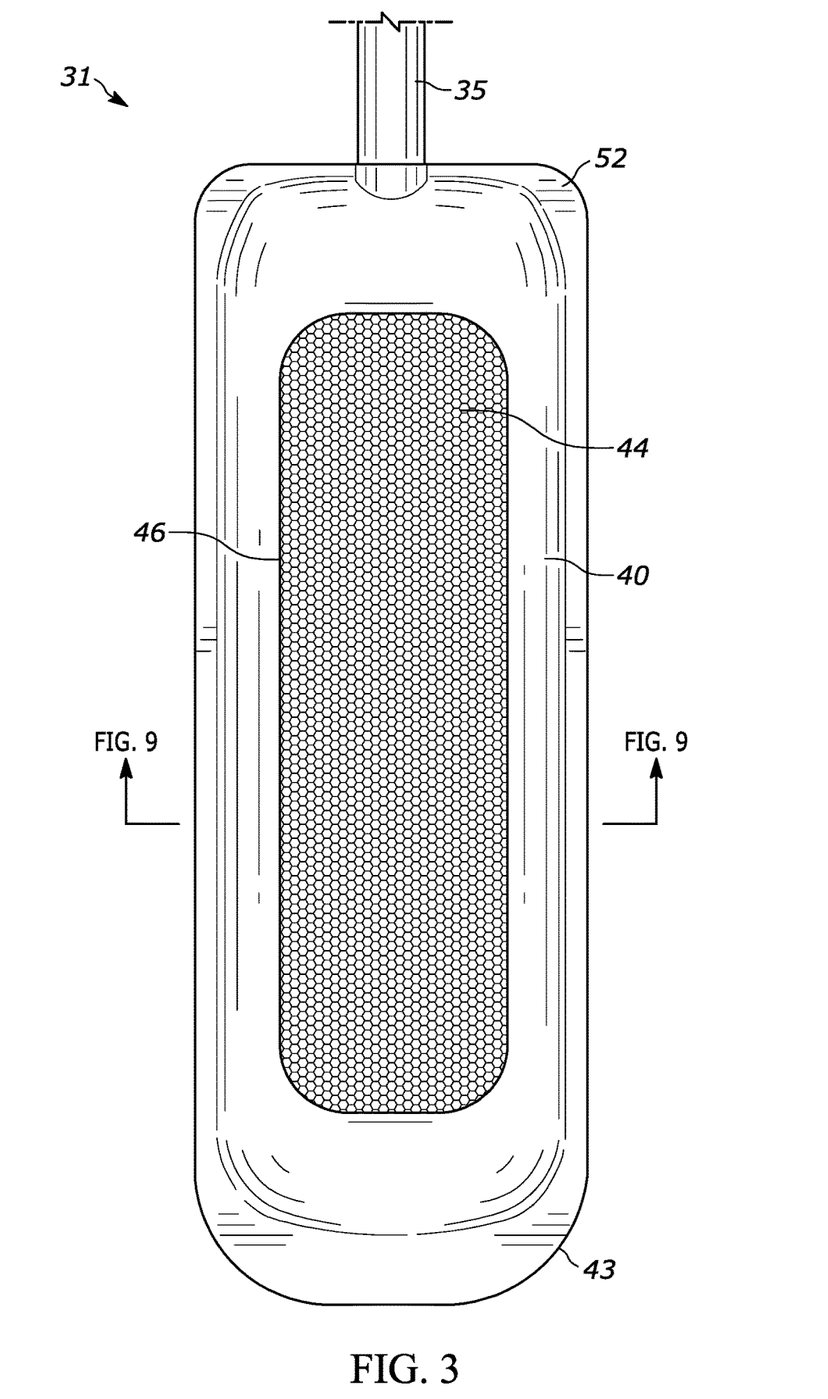
FIG. 3 is a front elevational view of the urinary collection device illustrated in the previous figures.

As described in U.S. Pat. No. 10,151,054, incorporated herein by reference, the core material can comprise a spacer knit fabric formed via joining two-dimensional knit fabric layers via knitted spacer threads or fibers. The first and second knit fabric layers may be the same or different, and each may comprise a knit, roughly honeycomb type structure as best illustrated in FIG. 3. As seen in FIG. 9, the plurality of fibers 62 extend from an obverse to a reverse position to thereby result in fluid permeability from the obverse to the reverse direction. The fibers generally form interstitial flow channels through the core, operating with the generally honeycomb-shaped fabric layers to allowing urine to flow easily from the obverse to the reverse direction, where it may be aspirated by suction in the tube 35. The tube 35 may have pores, but otherwise the density of the core is sufficiently low for urine to pool near the bottom region 59 (FIG. 4) of the core, which is disposed proximal an end of the tube such that the tube may quickly aspirate urine from the device.

The core may be composed of any suitable material, but preferably is composed of a polymer having a water contact angle arranging from 70-85°, such as a polyester. In preferred embodiments, the core comprises polyethylene terephthalate. A core as heretofore described is not very water-absorbent, such that urine can be guided through the core without being substantially retained within the core by absorption. This is particularly so when the core is fashioned of polyethylene terephthalate, which does not appreciably retain urine that enters the device 31 via the obverse face 40.

Generally, the core material may be characterized via the density of the fibers and the overall fluid permeability. Where the density of the fibers is too small, or the surface is too rough, this is believed to lead to patient discomfort and also to lead to the potential for urine spillage. Where the density of the fibers is too great, the suction applied to the tube 35 may not be sufficient to aspirate fluid from the urinary collection device.

Figure 4:
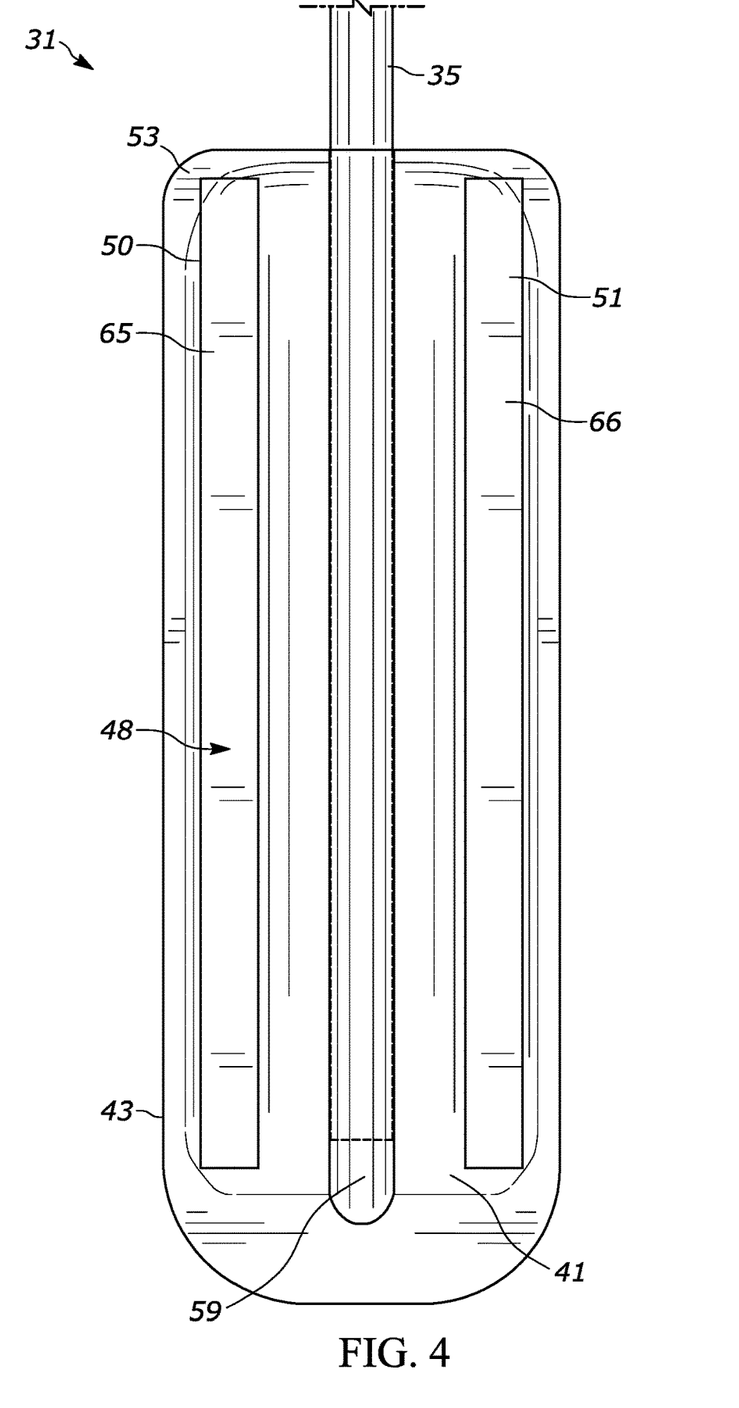
FIG. 4 is a rear elevational view of the urinary collection device illustrated in the previous figures.
Figure 5:
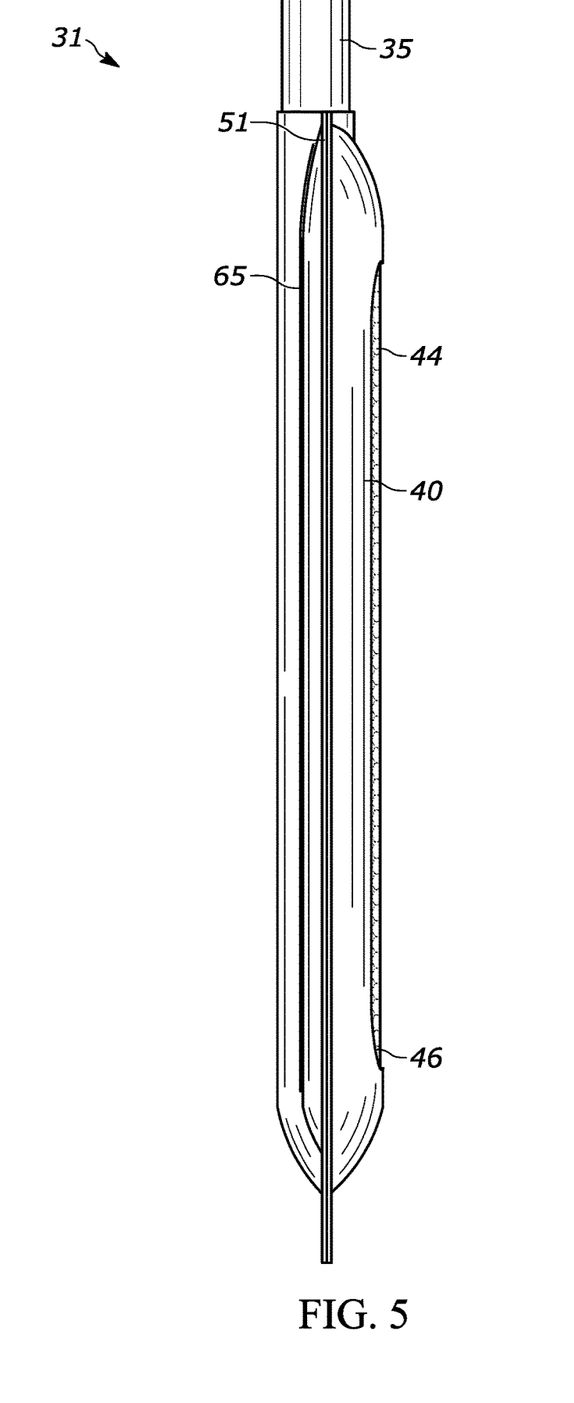
FIG. 5 is a left side elevational view of the urinary collection device illustrated in the previous figures.
Figure 6:
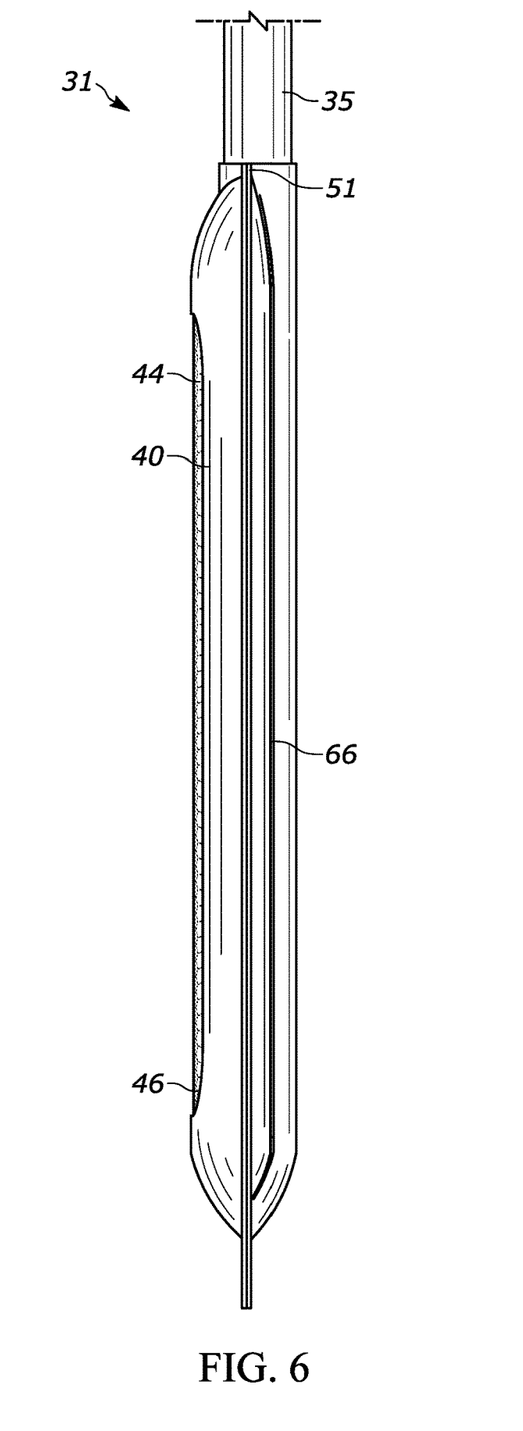
FIG. 6 is a right side elevational view of the urinary collection device illustrated in the previous figures.
Figure 7:
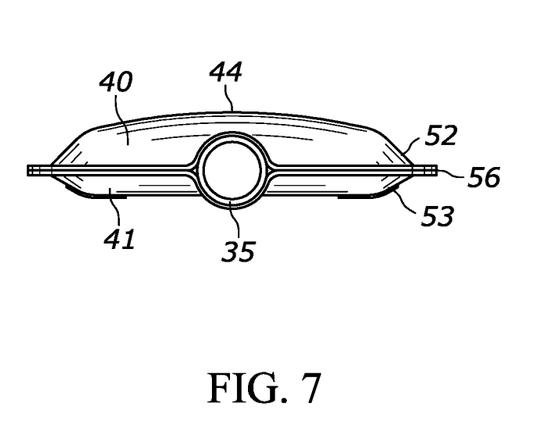
FIG. 7 is a top plan view of the urinary collection device illustrated in the previous figures.
Figure 8:
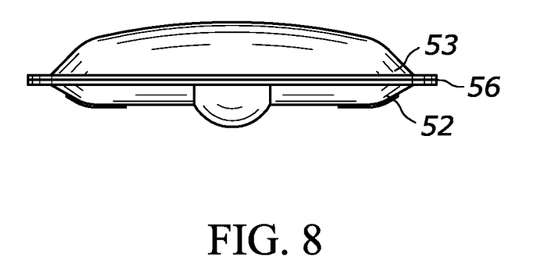
FIG. 8 is a bottom plan view of the urinary collection device illustrated in the previous figures.
Figure 11:
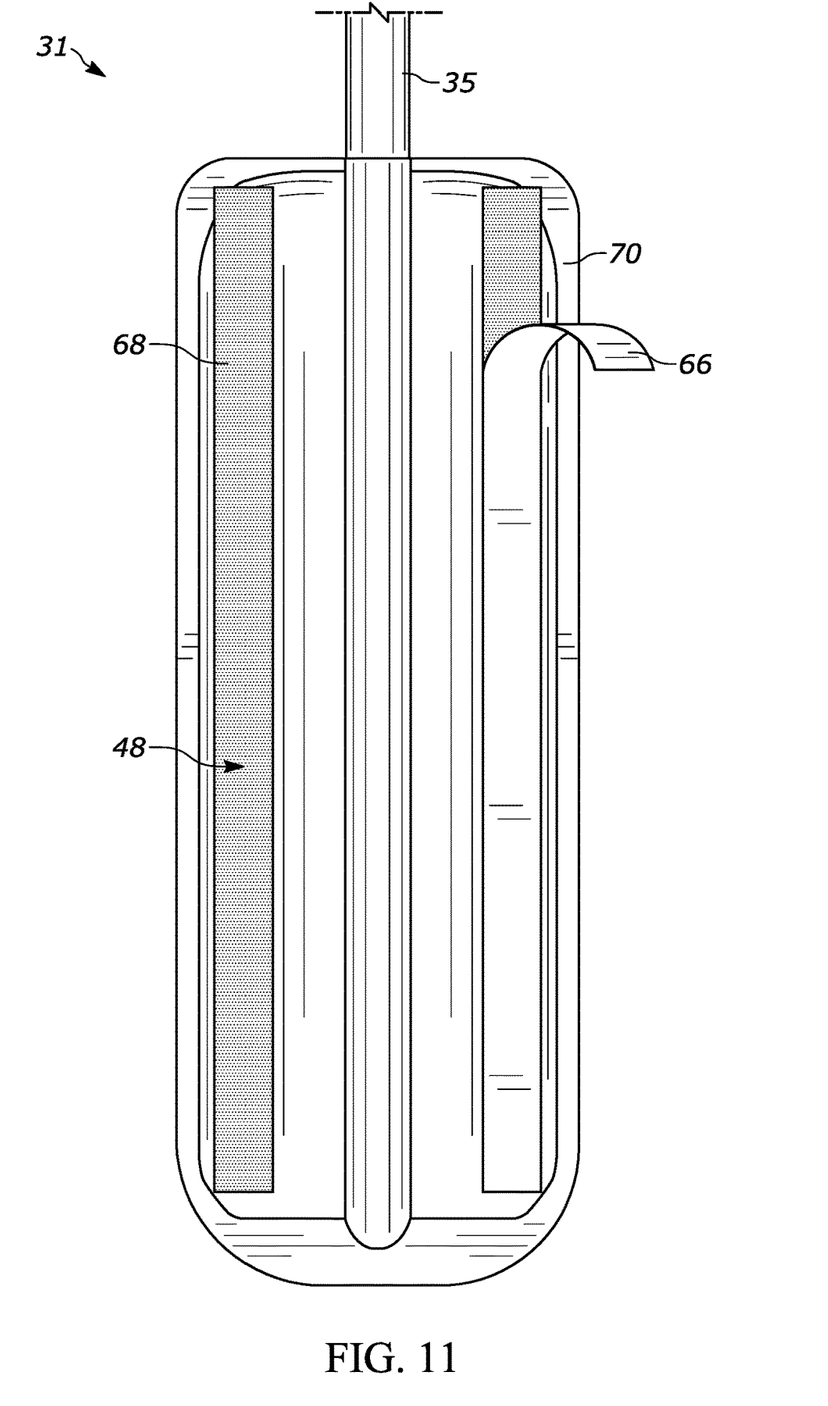
FIG. 11 is a rear elevational view of the urinary collection device illustrated in the previous figures, showing adhesive backing of the adhesive strips of the device removed.
Figure 12:
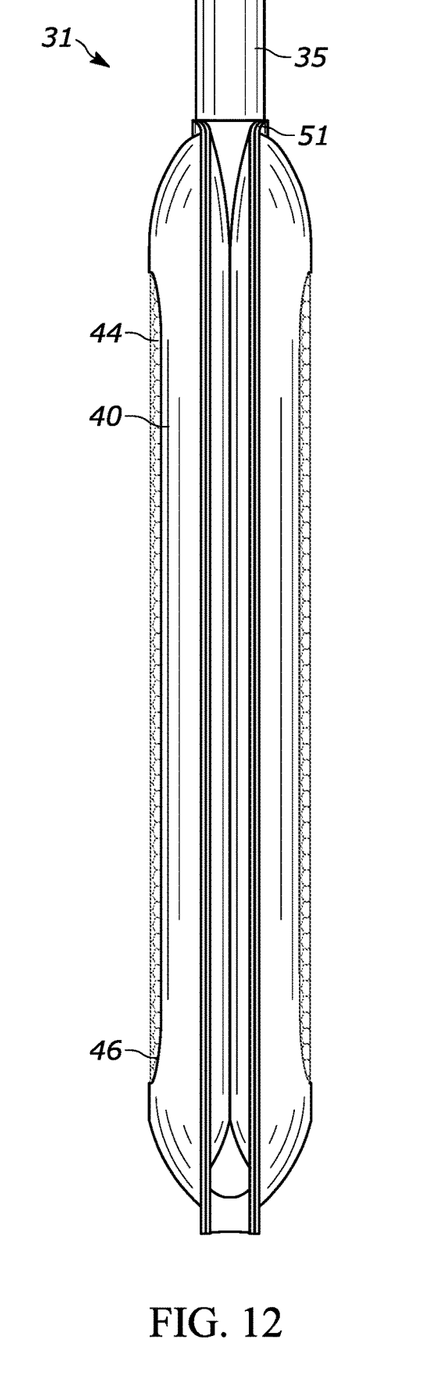
FIG. 12 is a rear elevational view of the urinary collection device folded such that the adhesive strips are attached to one another to thereby secure the device in a folded configuration.
Figure 13:
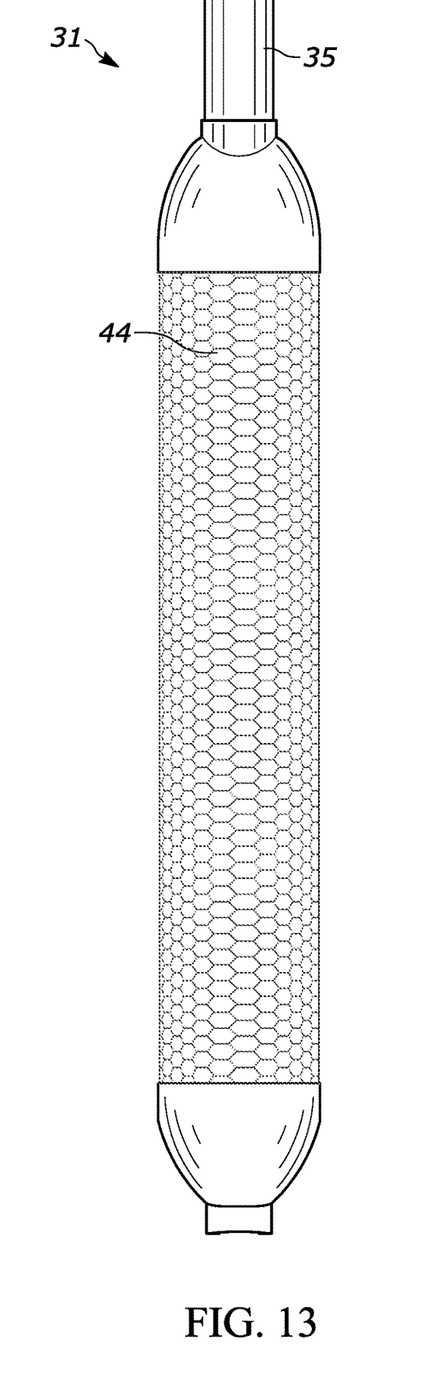
FIG. 13 is a front elevational view of the urinary collection device in the folded configuration.

The above device is suitable for supralabial positioning proximal a patient for urine collection. With reference to FIGS. 4 and 11, and as noted above, the device 31 includes an actuatable fastener 48, configured in the illustrated embodiment as a pair of backed adhesive strips 50, 51, disposed on the reverse face 41 of the device 31. When the backing material 65, 66 (FIG. 4) is removed to expose the adhesive 68, 70 on each strip (FIG. 11), the clinician may fold the device in a reverse-folded manner to bring the adhesive strips into contact with one another and to cause the adhesive strips to adhere to one another, as illustrated in FIGS. 12 and 13. Although the fastener is depicted as a pair of adhesive strips, it is contemplated that other actuatable fasteners, such as hook-and-loop fasteners or other suitable fasteners, may be employed, the fastener being non-actuated when supralabial positioning is intended and actuated for retention in the folded configuration for intralabial positioning.

Figure 14:
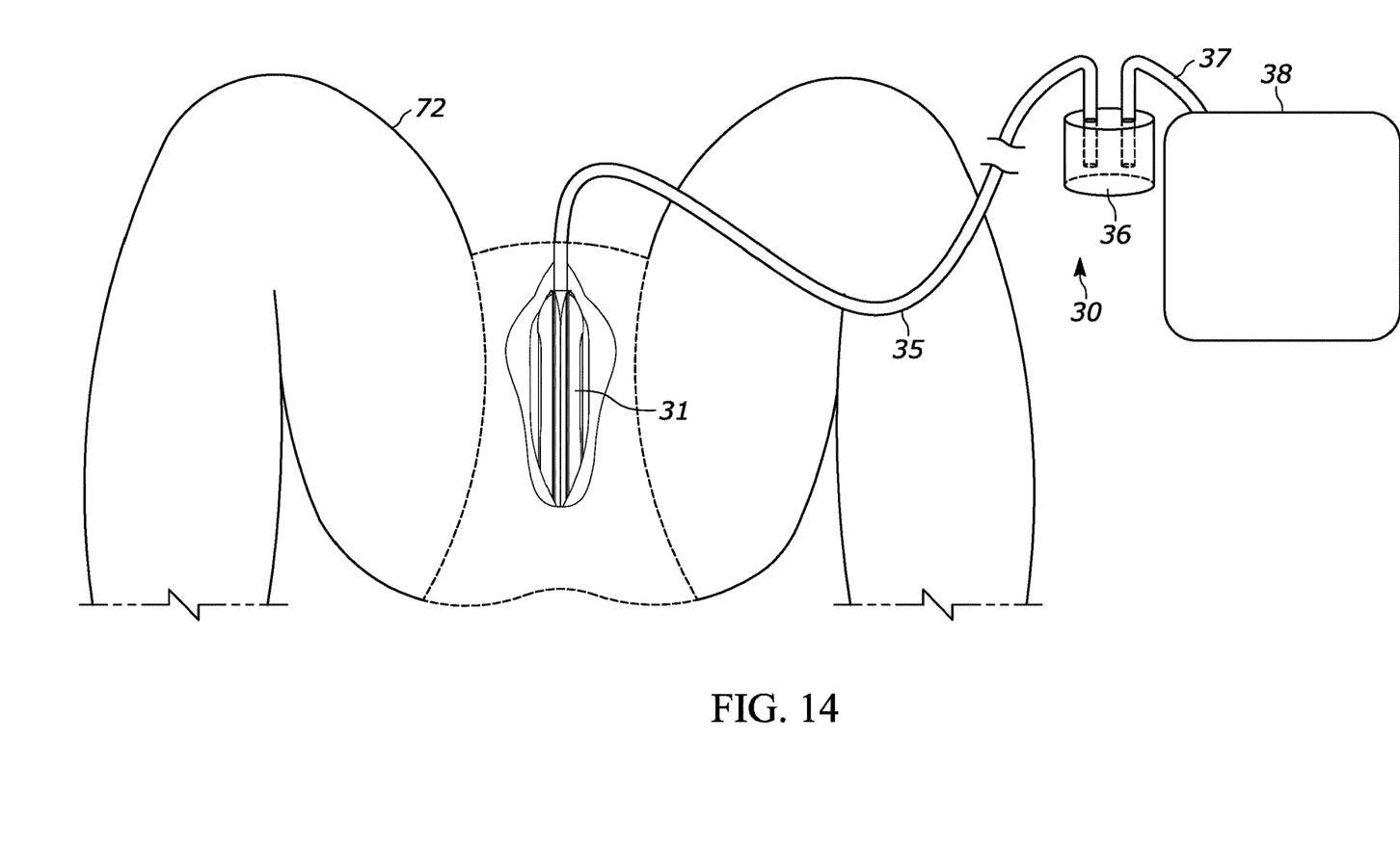
FIG. 14 is a perspective view illustrating the urinary collection device in the folded configuration and positioned within the labia of the female patient.

When in a folded configuration as illustrated in FIGS. 12 and 13, the urinary collection device 31 is suitable for intralabial positioning proximal a patient, as illustrated in FIG. 14 with respect to a patient 72, the patient 72 having relatively large labia or labial lips as compared to the patient 32 illustrated in FIG. 1. The fastener 48 is configured to retain the device in a reverse folded intralabial position upon actuation. As illustrated in FIG. 14, patients who present with relatively large labia are most suited for intralabial urine collection, whereas patients with relatively small labial lips are best suited for supralabial urine collection as shown in FIG. 1. In practice, a clinician may evaluate a patient to determine whether to employ supralabial or intralabial urine collection. Via the above disclosure, the clinician may place the urinary collection device proximal the patient for urine collection, placing the device in a supralabial position if supralabial urine collection is elected and, if and only if intralabial collection is elected, actuating the fastener and folding the device to retain the device in the reverse-folded intralabial position. The device thereby provides the option for the clinician to employ either supralabial or intralabial urine collection. As seen with reference to FIGS. 1 and 14, the device may be placed supralabially or intralabially for urine collection as appropriate.

Figure 15:
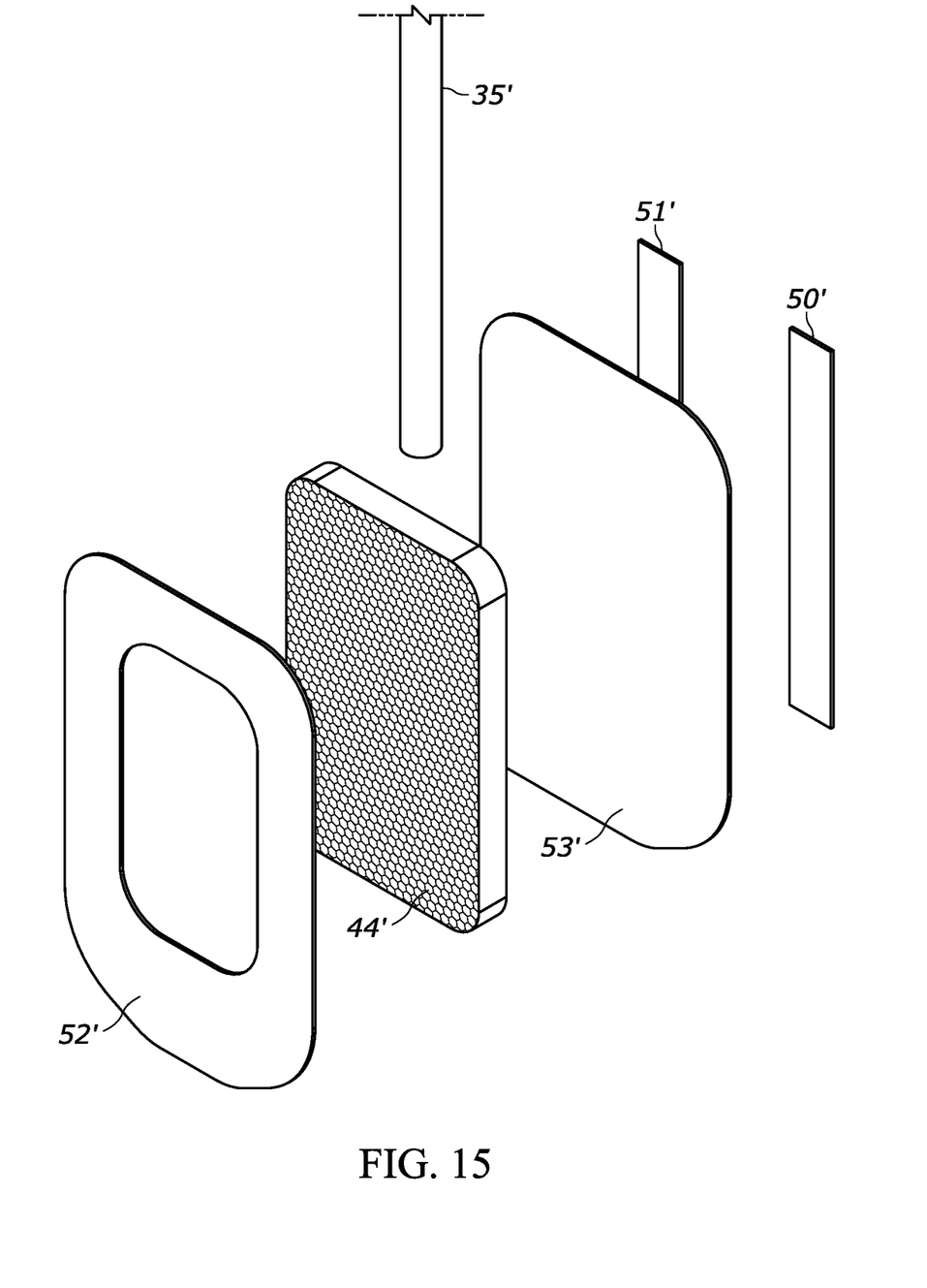
FIG. 15 is an exploded view of an alternative urinary collection device.

The device may be assembled via conventional assembly techniques and, the assembly method may comprise purchasing or preparing suitable core material, PVC tubing, and outer shell materials and gluing them in the order generally illustrated in FIG. 10. Instead of using internal adhesives to assemble the device, other suitable sealing techniques, such as ultrasonic welding, may be employed in suitable cases. The alternative embodiment illustrated in FIG. 15 contemplates such techniques with no internal adhesive connecting obverse outer layer 52', reverse outer layer 53', (but still including backed adhesive strips 50', 51') and having core 44' and tube 35' whose functions are as described above.

As seen in FIG. 1, if the adhesive strips are not used to retain a device in a reverse-folded configuration, the adhesive strips may be used to secure the device to the patient's undergarment 33.

It is thus seen that a versatile urine collection device, system, and method provided in various embodiments of the disclosure.

All methods described herein can be performed in any suitable order unless otherwise indicated herein or otherwise clearly contradicted by context. The use of any examples or exemplary language is intended to be exemplary and not to pose a limitation on the scope of the claims. Any statement herein as to the nature or benefits of the invention or of the preferred embodiments is not intended to be limiting. The claims are intended to cover all modifications and equivalents as permitted by applicable law. Any combination of the above-described elements in all possible variations thereof is encompassed by the invention unless otherwise indicated herein or otherwise clearly contradicted by context. The identification herein of any reference or patent, even if identified as "prior," is not intended to constitute a concession that such reference or patent is available as prior art against the present invention. The identification of any patent is not intended as a concession that the claims of such patent cover any of the heretofore-described embodiments. No unclaimed language should be deemed to limit the invention in scope. Any statements or suggestions herein that certain features constitute a component of the claimed invention are not intended to be limiting unless reflected in the appended claims. Neither the marking of the patent number on any product nor the identification of the patent number in connection with any service should be deemed a representation that all embodiments described herein are incorporated into such product or service.

What is claimed is:

1. A urinary collection device comprising:
    a generally fluid-impermeable outer surface having an obverse face and an obverse opening through the obverse face to allow urine to flow beyond the obverse face;
    a reverse face including a fastener configured to retain the urinary collection device in a reverse-folded intralabial position;
    an aspiration conduit extending longitudinally between the outer surface and the reverse face; and
    a generally fluid-permeable core between the outer surface and the reverse face, the core in fluidic communication with the aspiration conduit, wherein the core comprises a first knit fabric layer and a second knit fabric layer joined by a plurality of fibers, the fibers being oriented generally to extend from an obverse to a reverse position to thereby result in flow channels through the core, wherein the aspiration conduit is received to extend longitudinally between the second knit fabric layer and an inner surface of the reverse face.

2. The urinary collection device of claim 1 wherein the aspiration conduit extends longitudinally between the reverse face and the core.

3. The urinary collection device of claim 1 wherein the aspiration conduit extends longitudinally along an inner surface of the reverse face.

4. The urinary collection device of claim 1 wherein the aspiration conduit extends longitudinally along a reverse layer of the core.

5. The urinary collection device of claim 1 wherein the aspiration conduit extends longitudinally along an inner surface of the reverse face and along a reverse layer of the core.

6. The urinary collection device of claim 1 wherein in the reverse-folded intralabial position, the aspiration conduit extends longitudinally between folded portions of the core and folded portions of the outer surface.

7. The urinary collection device of claim 1 wherein the core is exposed through the obverse opening to allow urine to receive urine through the obverse opening.

8. The urinary collection device of claim 1 wherein the fastener comprises elongated strips spaced opposite the longitudinally-extending aspiration conduit.

9. The urinary collection device of claim 1 wherein the core compresses between the first and second knit fabric layers when the aspiration conduit is received between the second knit fabric layer and the reverse face.

10. A system comprising the urinary collection device of claim 1 and a source of suction connected to the aspiration conduit.

\* \* \* \* \*